US006559300B1

(12) United States Patent
Simon et al.

(10) Patent No.: US 6,559,300 B1
(45) Date of Patent: May 6, 2003

(54) WATER-SOLUBLE BIODEGRADABLE HYDROXYALKYL CELLULOSE-2-HYDROXYCARBOXYLIC ACID ESTERS WHICH CAN FLOCCULATE

(75) Inventors: Joachim Simon, Düsseldorf (DE); Hanns-Peter Müller, Odenthal (DE); Rainhard Koch, Köln (DE); Volkhard Müller, Bomlitz (DE); Jürgen Engelhardt, Leverkusen (DE); Klaus Szablikowski, Walsrode (DE); Wolfgang Koch, Bomlitz (DE)

(73) Assignee: Wolff Walsrode AG, Walsrode (DE)

( * ) Notice: Subject to any disclaimer, the term of this patent is extended or adjusted under 35 U.S.C. 154(b) by 0 days.

(21) Appl. No.: 09/462,730

(22) PCT Filed: Jul. 10, 1998

(86) PCT No.: PCT/EP98/04301

§ 371 (c)(1),
(2), (4) Date: Jan. 11, 2000

(87) PCT Pub. No.: WO99/05178

PCT Pub. Date: Feb. 4, 1999

(65) Prior Publication Data
(65)

(30) Foreign Application Priority Data

Jul. 23, 1997 (DE) .......................................... 197 31 575

(51) Int. Cl.⁷ .......................... C08B 3/00; C08B 13/00; C08B 11/08; C07H 15/04; C07H 1/00
(52) U.S. Cl. .............................. 536/63; 536/66; 536/95; 536/96; 536/116; 536/124

(58) Field of Search ............................... 536/95, 96, 63, 536/66, 116, 124

(56) References Cited

U.S. PATENT DOCUMENTS

| 4,443,595 A | | 4/1984 | Namikoshi et al. ........... 536/58 |
| 5,166,333 A | * | 11/1992 | Breckwoldt |
| 5,817,728 A | * | 10/1998 | Higuchi et al. |
| 5,861,506 A | * | 1/1999 | Simon et al. .................. 536/66 |

OTHER PUBLICATIONS

Journal of Polymer Science: Part A–1, vol. 6, (month unavailable) 1968, pp. 1705–1718, M.G. Wirick, Study of the Substitution Pattern of Hydroxyethylcelluose and its Relationship to Enzymic Degradation.

* cited by examiner

Primary Examiner—James O. Wilson
Assistant Examiner—Everett White
(74) Attorney, Agent, or Firm—Godfried R. Akorli; James R. Franks

(57) ABSTRACT

A water-soluble, biodegradable hydroxyalkyl cellulose-2-hydroxycarboxylic acid ester is disclosed. The hydroxyalkyl cellulose-2-hydroxycarboxylic acid ester has: (i) a molecular degree of substitution of the hydroxyalkyl group of less than 1.5 ($MS_{hydroxyalkyl}<1.5$); and (ii) a molecular degree of substitution of the 2-hydroxycarboxylic acid group of greater than 0.4 and less than 3 ($0.4<MS_{2-hydroxycarboxylic\ acid}<3$). Also described is a method of preparing the hydroxyalkyl cellulose-2-hydroxycarboxylic acid ester, and methods of using it, e.g., as a consistency regulator in at least one of foodstuffs, cosmetics, building materials, paints and strippers.

9 Claims, No Drawings

WATER-SOLUBLE BIODEGRADABLE HYDROXYALKYL CELLULOSE-2-HYDROXYCARBOXYLIC ACID ESTERS WHICH CAN FLOCCULATE

CROSS REFERENCE TO RELATED PATENT APPLICATIONS

The present patent application claims the right of priority under 35 U.S.C. §119 (a)·(d) and 35 U.S.C. §365 of International Application No. PCT/EP98/04301, filed Jul. 10, 1998, which was published in German as International Patent Publication No. WO 99/05178 on Feb. 4, 1999, which is entitled to the right of priority of German Patent Application Number 197 31 575.5, filed Jul. 23, 1997.

FIELD OF THE INVENTION

The present invention relates to novel water-soluble, thickening, thermoplastic, film-forming and rapidly biodegradable cellulose ether lactates.

BACKGROUND OF THE INVENTION

The biodegradability of a polysaccharide derivative is dependent on the degree of substitution of each saccharide unit [c.f. j. G. Batelaan in The Handbook of Environmental Chemistry, Volume 3, Part F, Ed. O. Hutzinger, Springer Verlag; 1992, 229–336; M. G. Wirick, Journal of Polymer Science, Part A-1, 6 (1968), 1705–1718]. Thus, all industrially available cellulose derivatives are rapidly biodegradable only if they have average degrees of substitution of less than 1.0. However, non-ionic cellulose ethers only become water-soluble with average degrees of substitution >>1. The known consistency regulators for aqueous systems based on non-ionic cellulose ethers such as, for example, methyl cellulose and hydroxyethyl cellulose, thus have degrees of substitution >1.5. Thickeners for organic solvents such as, for example, hydroxypropyl cellulose, even have degrees of substitution >2. Such compounds are only sparingly biodegradable (severe chemical oxygen demand).

SUMMARY OF THE INVENTION

The object of the present invention is to develop synthesis, performable on a fully industrial scale, of water- and/or organo-soluble cellulose derivatives which biodegrade quickly and completely.

According to the invention, this is achieved by reacting hydroxyalkyl cellulose ethers with a molecular degree of substitution with hydroxyalkyl groups of less than 1.5 ($MS_{hydroxyalkyl}<1.5$) to form hydroxyalkyl cellulose-2-hydroxycarboxylic acid esters with a molecular degree of substitution with 2-hydroxycarboxylic acid groups greater than 0.4 and less than 3 ($0.4<MS_{2-hydroxycarboxylic\ acid}<3$).

DETAILED DESCRIPTION OF THE INVENTION

Caellulose lactates are already known. In DE 33 22 118, cellulose esters are described, which are produced by reacting cellulose with lactide or glycolide in cellulose-specific solvent systems such as dimethylacetamide/LiCl. With this method, the synthesis is achieved of water-soluble cellulose-2-hydroxycarboxylic acid esters having a low degree of substitution, which may be used as coating agents or consistency regulators. However, use of the solvent system dimethylacetamide/lithium chloride is complex and not practicable on an industrial scale.

It has been established that hydroxyalkyl celluloses with degrees of substitution of less than 1 may be reacted in conventional organic solvents, such as for example dioxan, dimethylacetamide, N-methylpyrrolidone or tert-butyl alcohol, with glycolide or lactide, the cyclic dimer of lactic acid, to form water-soluble hydroxyalkyl cellulose-2-hydroxycarboxylic acid esters. Specific solvent systems for cellulose, such as for example N-methylmorpholine oxide or dimethylacetamide/lithium chloride are not necessary therefor. The underlying hydroxyalkylcellulose ethers are, according to the prior art, produced by alkalising a cellulose with aqueous sodium hydroxide solution and subsequent etherification with alkylene oxides.

Despite their high total degree of substitution, the hydroxyalkyl cellulose-2-hydroxycarboxylic acid esters biodegrade in aqueous solution markedly more quickly than alkyl and hydroxyalkyl cellulose ethers with comparable total degrees of substitution. The hydroxyalkyl cellulose-2-hydroxycarboxylic acid esters to be produced according to the invention may be described by the general structure (I)

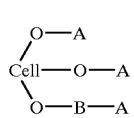

(I)

wherein Cell-O represents the substituted residue of a hydroxyl group on the cellulose chain and the groups A constitute a monomeric or oligomeric 2-hydroxycarboxylic acid of the structure (II)

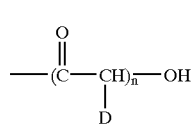

(II)

in which D stands for hydrogen (—H) or methyl (—CH$_3$) and n is a whole number between 0 and 10. B is a polymeric ether group of the general structure (III).

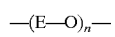

(III)

in which E stands for a branched or unbranched carbon chain with 2 to 6 C atoms and n is a whole number between 0 and 10. For all the groups A which do not correspond to the structure (II), A is hydrogen (—H).

To synthesise this hydroxyalkyl cellulose-2-hydroxycarboxylic acid ester, the hydroxyalkyl cellulose ether is suspended in an organic solvent and a reactive 2-hydroxycarboxylic acid derivative is added thereto. The reaction time is from 1 to 10 hours at reaction temperatures of between 50° C. and 150° C., preferably between 80° C. and 130° C.

Suitable cellulose ethers are, for example, hydroxyethyl cellulose, hydroxypropyl cellulose, hydroxybutyl cellulose and mixed ethers thereof with degrees of substitution ($MS_{hydroxyalkyl}$) of between 0.1 and 1.5, preferably between 0.5 and 1.0.

Suitable 2-hydroxycarboxylic acid derivatives are the cyclic dimers glycolide, L-, D- and meso-lactide as well as lactic acid esters and lactic acid oligomers with from 2 to 10 repeat units.

Suitable suspending agents or solvents are polar aprotic compounds such as, for example, dimethylformamide, dimethylacetamide, dioxan, tetrahydrofuran, N-methylmorpholine, N-methylpyrrolidone, dimethoxymethane, dimethyl ether, diethylene glycol dimethyl ether and, in addition, protic solvents such as, for example, tert-butyl alcohol. The reaction may also be performed without solvent in a lactide melt. The cellulose ether esters according to the invention are water-soluble and make good film formers. As the degree of substitution with hydroxyalkyl and -hydroxycarboxylic acid groups increases, the products additionally become organo-soluble and melt processable.

Hydroxyethyl and hydroxypropyl cellulose lactates, the sum of the degrees of substitution of which with hydroxyalkyl and lactic acid groups exceeds 1.5 ($\Sigma MS_{lactate}$ and $MS_{hydroxyalkyl}$>1.5) are only water-soluble below a certain temperature. Above this temperature (flocculation temperature), the hydroxyalkyl cellulose lactates precipitate out of an aqueous solution. This flocculation temperature is dependent on the degree of substitution of the cellulose ether esters. By varying the degrees of substitution with lactate and hydroxyalkyl groups, a thermal flocculation point of the hydroxyalkyl cellulose lactates of between 30° C. and 75° C. may be established. At degrees of substitution with lactate groups greater than 3 ($MS_{lactate}$>3), the flocculation point drops below room temperature. The products are then insoluble in both cold and hot water.

The products may be used for all applications for which water-soluble biodegradable products are suitable. Thus, for example, they may be used as consistency regulators for foodstuffs, cosmetics, building materials, paints and strippers or for producing microcapsules for the foodstuffs, crop protection and pharmaceutical sectors.

The degrees of substitution may be determined with conventional methods of cellulose derivative analysis, such as, for example, Zeisel cleavage, elementary analysis, gas chromatography and $^{13}C$ NMR spectroscopy. The property of biodegradability claimed according to the invention is investigated using the Zahn-Wellens test, DIN EN 29 888.

The subject matter of the present invention is explained in still more detail with the aid of the present Examples.

EXAMPLE 1

A hydroxypropyl cellulose (75 g/0.36 mol) with a molar degree of substitution ($MS_{hydroxypropyl}$) of 0.92 is suspended in 691 ml dimethylacetamide and heated to 130° C. After the addition of 25 g (0.18 mol) L-lactide, stirring is performed for 5 hours. The resultant pasty composition is stirred into acetone and, as it precipitates, the product is isolated, washed and dried. 89 g hydroxypropyl cellulose lactate are obtained.
$MS_{lactate}$: 0.6
$V_2$(water): 413 mPas
Biodegradation: 78%
Softening point: 170° C.

EXAMPLE 2

A hydroxypropyl cellulose (75 g/0.36 mol) with a molar degree of substitution ($MS_{hydroxypropyl}$) of 0.92 is suspended in 691 ml dimethylacetamide and heated to 130° C. After the addition of 75 g (0.52 mol) L-lactide, stirring is performed for 5 hours. The resultant pasty composition is stirred into acetone and, as it precipitates, the product is isolated, washed and dried. 100 g hydroxypropyl cellulose lactate are obtained.
$MS_{lactate}$: 1.0
$V_2$(water): 307 mPas
Flocculation point: 59° C.
Biodegradation: 71%

EXAMPLE 3

A hydroxypropyl cellulose (75 g/0.36 mol) with a molar degree of substitution ($MS_{hydroxypropyl}$) of 0.92 is suspended in 691 ml dimethylacetamide and heated to 130° C. After the addition of 104 g (0.72 mol) L-lactide, stirring is performed for 5 hours. The resultant pasty composition is stirred into acetone and, as it precipitates, the product is isolated, washed and dried. 110 g hydroxypropyl cellulose lactate are obtained.
$MS_{lactate}$: 1.5
$V_2$(water): 153 mPas
Flocculation point: 35° C.
Biodegradation: 80%
Softening point: 170° C.

EXAMPLE 4

Aqueous lactic acid (85%) is condensed at temperatures >180° C. under a vacuum for 4 hours to form oligomers. The acid value then amounts to <100, corresponding to oligomers of lactic acid with average degrees of oligomerisation of from 4–8. 10.8 g of the lactic acid oligomers were reacted with 8 g (0.04 mol) of a hydroxypropyl cellulose with a molar degree of substitution of 0.82 ($MS_{HP}$ 0.82) in DMAc at 120° C. After removal of the solvent, 14 g of HPC lactate are isolated.
$MS_{lactate}$: 2.0
Softening point: 170° C.

EXAMPLE 5

A hydroxyethyl cellulose (75 g/0.40 mol) with a molar degree of substitution ($MS_{hydroxypropyl}$) of 0.68 is suspended in 691 ml N-methylpyrrolidone and heated to 130° C. After the addition of 87 g (0.60 mol) L-lactide, stirring is performed for 5 hours. The resultant pasty composition is stirred into acetone and, as it precipitates, the product is isolated, washed and dried. 90 g hydroxyethyl cellulose lactate are obtained.
$MS_{lactate}$: 1.8
$V_2$(water): 956 mPas
Flocculation point: 35° C.
Biodegradation: 80%

COMPARATIVE EXAMPLES hydroxyethyl cellulose
$MS_{hydroxyethyl}$: 2.5
Biodegradation: 13%
Hydroxypropyl cellulose
$MS_{hydroxypropyl}$: 4.0
Biodegradation: 22%

What is claimed is:
1. A biodegradable hydroxyalkyl cellulose-2-hydroxycarboxylic acid ester having:
   (i) a molecular degree of substitution of the hydroxyalkyl group of less than 1.5 ($MS_{hydroxyalkyl}$<1.5); and
   (ii) a molecular degree of substitution of the 2-hydroxycarboxylic acid, group of greater than 0.4 and less than 3 (0.4<$MS_2$-hydroxycarboxylic acid<3), provided that said biodegradable hydroxyalkyl cellulose-2-hydroxycarboxylic acid ester is water-soluble.
2. The water-soluble, biodegradable hydroxyalkyl cellulose-2-hydroxycarboxylic acid ester of claim 1 wherein, (i) the hydroxalkyl group is selected from the group consisting of hydroxyethyl, hydroxypropyl and hydroxybutyl, and (ii) the 2-hydroxycarboxylic acid group is selected from the group consisting of monomeric glycolate, oligomeric glycolate, D-lactate and L-lactate.

3. The water-soluble, biodegradable hydroxyalkyl cellulose-2-hydroxycarboxylic acid ester of claim 2 wherein the hydroxyalkyl group is hydroxypropyl, and the 2-hydroxycarboxylic acid group is selected from one of D-lactate and L-lactate, the sum of the molecular degrees of substitution with lactate and hydroxypropyl groups is greater than 1.5 ($\Sigma Ms_{lactate}$ and $Ms_{hydroxyalkyl}$>1.5), said hydroxyalkyl cellulose-2-hydroxycarboxylic acid ester being insoluble in hot water.

4. The water-soluble, biodegradable hydroxyalkyl cellulose-2-hydroxycarboxylic acid ester of claim 1 wherein said hydroxyalkyl cellulose-2-hydroxycarboxylic acid ester is a hydroxyalkyl cellulose lactate having a thermal flocculation point of between 30° C. and 75° C.

5. A method of preparing the water-soluble, biodegradable hydroxyalkyl cellulose-2-hydroxycarboxylic acid ester of claim 1 comprising, reacting, (a) a hydroxyalkyl cellulose ether having a molecular degree of substitution of the hydroxyalkyl group of less than 1.5 ($MS_{hydroxyalkyl}$<1.5), with (b) at least one of, (i) a cyclic 2-hydroxycarboxylic acid dimer selected from the group consisting of glycolide, L-lactide, D-lactide and meso-lactide, (ii) lactic acid esters, and (iii) lactic acid oligomers having 2 to 10 repeat units.

6. The method of claim 5 wherein said hydroxyalkyl cellulose ether has a molecular degree of substitution of the hydroxyalkyl group of between 0.1 and 1.5 (0.1<$MS_{hydroxyalkyl}$<1.5).

7. The method of claim 5 wherein said hydroxyalkyl cellulose ether has a molecular degree of substitution of the hydroxyalkyl group of between 0.5 and 1.0 (0.5<$MS_{hydroxyalkyl}$<1.0).

8. A method of preparing foodstuffs, cosmetics, building materials, paints and strippers comprising:

(a) providing the water-soluble, biodegradable hydroxyalkyl cellulose-2-hydroxycarboxylic acid ester of claim 1; and (b) incorporating said water-soluble, biodegradable hydroxyalkyl cellulose-2-hydroxycarboxylic acid ester as a consistency regulator In at least one of foodstuffs, cosmetics, building materials, paints and strippers.

9. A method of preparing microcapsules comprising:

(a) providing the water-soluble, biodegradable hydroxyalkyl cellulose-2-hydroxycarboxylic acid ester of claim 1; and (b) producing microcapsules with said water-soluble, biodegradable hydroxyalkyl cellulose-2-hydroxycarboxylic acid ester.

* * * * *